United States Patent
Ishibashi et al.

(10) Patent No.: US 6,231,343 B1
(45) Date of Patent: May 15, 2001

(54) METHOD FOR BLEACHING DISCOLORED TOOTH BY TITANIUM DIOXIDE PHOTOCATALYST

(75) Inventors: Takuro Ishibashi; Kouzo Ishibashi, both of 157-7, Oaza-Koura Izuhara-machi, Shimoagata-gun, Nagasaki 817-0001; Hiroshi Taoda, 33, Kiyozumi-cho 1-chome, Chikusa-ku, Nagoya-shi, Aichi 464-0034; Toru Nonami, 9-6, Kibogaoka 3-chome, Chikusa-ku, Nagoya-shi, Aichi 464-0016, all of (JP)

(73) Assignees: Japan as represented by Director General of Agency of Industrial Science and Technology, Tokyo; Takuro Ishibashi; Kouzo Ishibashi, both of Shimoagata-gun; Hiroshi Taoda; Toru Nonami, both of Nagoya, all of (JP)

( * ) Notice: Subject to any disclaimer, the term of this patent is extended or adjusted under 35 U.S.C. 154(b) by 0 days.

(21) Appl. No.: 09/508,109

(22) PCT Filed: Sep. 18, 1998

(86) PCT No.: PCT/JP98/04220

§ 371 Date: Jun. 9, 2000

§ 102(e) Date: Jun. 9, 2000

(87) PCT Pub. No.: WO99/15143

PCT Pub. Date: Apr. 1, 1999

(30) Foreign Application Priority Data

Sep. 19, 1997 (JP) .................................................. 9-273650

(51) Int. Cl.$^7$ ..................................................... A61C 5/00
(52) U.S. Cl. ............................................ 433/215; 433/216
(58) Field of Search ..................................... 433/215, 216, 433/229, 80

(56) References Cited

U.S. PATENT DOCUMENTS

| | | | |
|---|---|---|---|
| 5,766,574 | * | 6/1998 | Christina-Beck et al. ............. 424/53 |
| 5,902,568 | * | 5/1999 | Ryles et al. ............................. 424/53 |
| 5,914,305 | * | 6/1999 | Madison et al. ...................... 510/367 |

* cited by examiner

Primary Examiner—Nicholas D. Lucchesi
(74) Attorney, Agent, or Firm—Oblon, Spivak, McClelland, Maier & Neustadt, P.C.

(57) ABSTRACT

The present invention relates to a method for bleaching a discolored tooth, comprising the steps of applying a solution/paste of titanium dioxide powder and hydrogen peroxide solution onto the surface of discolored teeth, and bleaching the tooth based on the photocatalytic action that is produced by irradiating this area with light; and to a bleaching agent for applying onto the surface of discolored tooth to bleach the discolored tooth based on the photocatalytic action that is produced by irradiating this area with light, the bleaching agent comprising as active ingredients a combination of hydrogen peroxide solution and titanium dioxide producing photocatalytic action when irradiated with light.

16 Claims, No Drawings

METHOD FOR BLEACHING DISCOLORED TOOTH BY TITANIUM DIOXIDE PHOTOCATALYST

BACKGROUND OF THE INVENTION

1. Field of the Invention

The present invention relates to the utilization of photocatalytic action to bleach and remove colored sediment on (stained or discolored) teeth, and more particularly to a method for bleaching discolored teeth comprising the steps of applying a bleaching agent comprising a specific composition having photocatalytic action on the surface of discolored teeth, and bleaching the teeth based on the photocatalytic action that is produced by irradiating this area with light; a novel bleaching agent comprising a solution/paste of 3% or less aqueous hydrogen peroxide and titanium dioxide producing photocatalytic action when irradiated with light, which is useful for such bleaching; a method for producing such a bleaching agent; and a bleaching system comprising a combination of the aforementioned bleaching agent and the like.

2. Description of the Related Art

There has been increasing demand in recent years for improvements in the contour, alignment, and integrity of teeth in dental therapy, which may be referred to as cosmetic improvements. Recently there have been more cases of patients seeking dental therapy based on a desire for whiter teeth, which is increasingly regarded by young women as an important element of beauty. The causes of dental discoloration and pigmentation or staining are generally classified into so-called extrinsic factors, such as the sedimentation of colored substances (tobacco, tea, etc.), pigment generating bacteria, the discoloration of repair materials (primarily composite resins), and metal salts (primarily amalgams, silver nitrate, and ammonia silver), and intrinsic factors, such as aging, chemicals or drugs (such as fluorine and tetracyclines), dysmetabolism and hereditary diseases, and dental injuries. The latter intrinsically discolored teeth are indicated for bleaching methods to which dental health system treatment is applied.

Several methods have been proposed in the past as methods for the cosmetic improvement of discolored teeth, among which bleaching may be considered a highly effective method for the preservation of dentine, despite drawbacks such as occasional recurrence, when methods suited to individual cases are selected and properly carried out.

Bleaching is essentially a method for decolorizing colored substances by means of a chemical reaction. In the past, there have been various reports of bleaching agents comprising a variety of chemical agents based on vital bleaches and non-vital bleaches, as well as bleaching methods involving the use of such agents.

The following are some typical examples.

1) Bleaching which features the use of 30% $H_2O_2$ as the chemical agent, and the combined use of light and heat on the aqueous hydrogen peroxide.

This is a method in which strips of gauze soaked in 30% $H_2O_2$ are placed on the front surface of the teeth and are irradiated for 30 minutes from the left and right by two 500 W photographic lamps. In this method, the lamps are brought as close as possible, and the $H_2O_2$ must be replenished about every 5 minutes to keep the gauze from drying.

2) Bleaching which features the use of 30% $H_2O_2$ as the chemical agent, and the concurrent use of high frequency current on the aqueous hydrogen peroxide.

This is a method in which strips of gauze soaked in 30% $H_2O_2$ are placed on the front surface of the teeth, and high frequency current is delivered for 1 second with the spoon-shaped tip of a high frequency scalpel. These operations are repeated 6 to 8 times every 8 seconds, during which time the $H_2O_2$ in the gauze must be replenished to prevent it from drying.

3) Bleaching in which a paste comprising Aerosil (silica fine powder) mixed with 35% $H_2O_2$ is used as the chemical agent, and the aqueous hydrogen peroxide and Aerosil paste is applied.

This is a method in which the aforementioned chemical agent is applied to the front surface of the teeth, which have been etched, the teeth are rinsed with water after 15 minutes, and they are then polished. In this method, the Aerosil serves as a moisturizing material to prevent the bleaching agent from drying out and further enhances the bleaching effects, resulting in high bleaching effects without the application of light or heat. The 35% $H_2O_2$ is highly corrosive and must therefore be handled with care.

4) Bleaching in which a paste obtained by kneading a 35% $H_2O_2$ solution and a powder (ingredients comprising potassium sulfate, manganese sulfate, silicone dioxide, or the like) is used as the chemical agent (Matsukaze Highlight, trademark).

In this method, the aforementioned chemical agent is placed on the front of the teeth and allowed to stand to bring about the action for 10 minutes thereof, or the material is irradiated with light for 3 minutes using a visible light ray radiation device. An advantage of this method is that the paste is a light green immediately after being kneaded but turns yellow when irradiated, and when the paste turns brown immediately after being kneaded, this indicates that the bleaching effects of the liquid have diminished. A drawback, however, is the same as that described above with the use of 35% $H_2O_2$.

5) Bleaching in which a mixture of 1 mL of 30% HCl, 1 mL of 30% $H_2O_2$, and 0.2 mL of diethyl ether is used as the chemical agent (improved MacInnes bleaching).

In this method, the aforementioned mixture is allowed to act for 5 minutes on the dental surface, and the teeth are then polished for 15 seconds under light pressure with a polishing disc. These operations are repeated 3 times, the material is then neutralized with 5.25% NaOCl, and the teeth are thoroughly rinsed with water (Oral Surg., 26: 871–878 (1968), J. Am. Dent. Assoc., 87:1329 (1973)). In this method, the paste can scatter into the eyes, making it necessary to adequately protect the patient's eyes.

6) A method in which a kneaded paste of 30% $H_2O_2$ and a sodium perborate powder is used as the chemical agent (working bleach method).

In this method, to dilate the dentinal canaliculus and enhance the bleaching effects, the walls in the pulp cavity are treated with phosphoric acid for 1 minute, rinsed with water, and dried, and the aforementioned paste is introduced into the pulp cavity and temporarily sealed with a cement. Although this method is currently widely used for clinical purposes to which health insurance is applied as a simple, highly effective bleaching method, a drawback is the same as that described above with the use of 30% $H_2O_2$.

Many other bleaching methods have also been reported, such as the dental bleaching agent and method comprising a mixture of aqueous hydrogen peroxide and ortho-phosphoric acid (Japanese Layed-Open Patent Application H8-143436/1996), the bleaching agent comprising a mixture of silicic anhydride with aqueous hydrogen peroxide, and the vital bleaching method comprising the application of such a bleaching agent (Japanese Layed-Open Patent Application H5-320033/1993), and the dental bleaching composition comprising a dental bleaching agent (such as hydrogen-urea peroxide, hydrogen peroxide-carbamide, and carbamide peroxide) and a matrix material (such as carboxymethylene), and a method for bleaching teeth using the above (Japanese Layed-Open Patent Application H8-113520/1996).

The following conditions are required of bleaching methods and bleaching agents during dental bleaching, however:

(a) pronounced bleaching effects;

(b) the use of chemical agents that are not toxic;

(c) ease of operations;

(d) avoidance of detracting from dental physical properties after treatment;

(e) effectiveness for both vital and non-vital methods; and (f) rapid bleaching effects.

A bleaching method fulfilling the above conditions would be capable of affording cosmetic improvement while preserving dental contour, with considerably improved effects.

In conventional bleaching methods, however, the primary chemical agent is 30 to 35% aqueous hydrogen peroxide, which is highly corrosive, and the oxidative action of which is the basis of bleaching.

All of the various bleaching methods currently used in Japan can be said to comprise, as noted above, a combination of 30 to 35% aqueous hydrogen peroxide, various utensils, and other chemical agents. There is an example of a bleaching method employed in the United States which features the use of 10% urea peroxide instead of 30 to 35% aqueous hydrogen peroxide, but this method is currently embroiled in controversy over problems in terms of efficacy and safety, and has yet to gain approval in Japan.

Bleaching methods covered as insured treatment are currently limited to pulpless teeth, and in some cases pulpectomy is performed on non-caries teeth for the purpose of bleaching. In addition, the use of highly toxic 30 to 35% aqueous hydrogen peroxide in various bleaching methods restricts operations and the like in a variety of ways, while limited bleaching effects for pulped teeth in particular have been indicated.

There is thus a strong need for the development of a safer, faster, simpler novel dental bleaching method that would be effective for both vital teeth and pulpless teeth.

SUMMARY OF THE INVENTION

The present invention is intended to provide a method for bleaching discolored teeth using a titanium dioxide photocatalyst.

The present invention relates to a method for bleaching discolored teeth, comprising the steps of applying a solution/paste of titanium dioxide powder and aqueous hydrogen peroxide to the surface of discolored teeth, and bleaching the teeth based on the photocatalytic action that is produced by irradiating this area with light; and also to a bleaching agent which is applied to the surface of discolored teeth to bleach the discolored teeth based on the photocatalytic action that is produced by irradiating this area with light, the aforementioned bleaching agent comprising as active ingredients a combination of aqueous hydrogen peroxide and titanium dioxide producing photocatalytic action when irradiated with light.

Characteristic effects afforded by the present invention include the following: (1) the ability to provide a novel bleaching agent for discolored teeth; (2) the ability to bleach both vital teeth and pulpless teeth; (3) higher safety, better workability, and rapid bleaching effects; (4) alleviation of mental distress on treated patients; (5) the ability to control the level of color adaptation; and (6) the ability to select improvements in color adaptation desired by the treated patient.

DISCLOSURE OF THE INVENTION

As a result of extensive research in light of the foregoing to establish a novel bleaching method that would be safer and simpler, and that would also afford better bleaching effects, the inventors perfected the present invention upon discovering that the intended objectives can be achieved by the combined use of active ingredients comprising aqueous hydrogen peroxide and titanium dioxide having photocatalytic action.

That is, an object of the present invention is to provide a safer, faster, simpler novel dental bleaching method that would be effective for both vital teeth and pulpless teeth.

A further object of the present invention is to provide a novel bleaching agent used in the aforementioned bleaching method, a method for its manufacture, and a system for bleaching teeth using the aforementioned bleaching agent.

The present invention resolving the aforementioned drawbacks comprises the following technical means:

(1) A method for bleaching a discolored tooth, comprising the steps of applying a solution/paste of a titanium dioxide powder and hydrogen peroxide solution onto the surface of the discolored tooth, and irradiating this area with light to bleach the tooth based on the resultant photocatalytic action.

(2) The method for bleaching a discolored tooth according to (1) above, wherein violet or blue visible light is irradiated.

(3) A bleaching agent for applying onto a surface of a discolored tooth to bleach the discolored tooth based on a photocatalytic action that is produced by irradiating this area with light, said bleaching agent comprising as active ingredients a combination of hydrogen peroxide solution and titanium dioxide which produces the photocatalytic action when irradiated with light.

(4) The bleaching agent according to (3) above, consisting of a solution/paste of titanium dioxide with a particle diameter of about 5 to 60 nm and 3% or less hydrogen peroxide solution.

(5) A method for producing a bleaching agent for applying onto a surface of a discolored tooth to bleach the discolored teeth based on the photocatalytic action that is produced by irradiating this area with light, said method for producing a bleaching agent comprising the step of blending hydrogen peroxide solution with a titanium dioxide powder producing photocatalytic action when irradiated with light.

(6) The method for producing a bleaching agent according to (5) above, comprising blending 3% or less hydrogen peroxide solution with a titanium dioxide powder producing photocatalytic action when irradiated with light.

(7) The method for producing a bleaching agent according to (5) or (6) above, wherein anatase-type titanium dioxide is arranged as the titanium dioxide powder.

(8) A system for bleaching tooth comprising a combination of a bleaching agent according to (3) or (4) above, means for applying said bleaching agent, irradiating means, and/or other dental treatment materials.

(9) The system for bleaching tooth according to (8) above, wherein a radiation device for generating visible violet light is combined.

The present invention is described in further detail below.

To achieve the objects of the present invention, the present invention provides high bleaching effects for discolored teeth, primarily through the oxidative and reductive action of the photocatalyst. In the present invention, the term discoloration is defined as expressing a broad range of meanings including staining.

The chemical agents and utensils used in the present invention may essentially comprise titanium oxide powder, aqueous hydrogen peroxide, and visible light rays (radiating instrument), affording considerable stability, ease of operation, and bleaching effects. The aforementioned aqueous hydrogen peroxide is more suitably used in lower concentrations, such as a concentration of 6% or less, and preferably a lower concentration of 3% or less.

In a preferred embodiment, the bleaching agent of the present invention is composed of a solution/paste of titanium dioxide powder and aqueous hydrogen peroxide in a low concentration of, for example, 6% or less (and preferably 3% or less). Examples of desirable titanium dioxide include, but are not limited to, titanium dioxide having a particle diameter of about 5 to 60 nm, and particularly anatase type titanium dioxide fine particles or materials based thereon. Any titanium dioxide having similar effects, that is, producing photocatalytic action, can be used, no matter what the shape or properties. Advantages of a smaller particle diameter in this case are that higher activity can be anticipated, good effects can be obtained with lower amounts, lower amounts can be used, high bleaching effects can be obtained more rapidly because thinner coating films can be used, for example, and so forth.

The weight ratio of the aforementioned ingredients can be adjusted as desired depending, for example, on whether the degree of discoloration is lighter or greater, so that products suited to individual cases can be prepared. The bleaching agent of the present invention is ordinarily, but not only, used in the form of a uniform transparent solution or paste by blending, kneading, and dispersing the titanium dioxide powder in aqueous hydrogen peroxide of low concentration. Any type that is prepared in a manner similar to this is encompassed within the range of the present invention. The term "solution/paste" as used in the present invention is defined as any having the aforementioned meaning. In this case, the means and devices for preparing the bleaching agent such as by blending, kneading, dispersion or otherwise manipulating the aforementioned ingredients, as well as the means and the like for applying the bleaching agent, are not particularly limited. Any suitable type can be used. An example of a desirable method for applying the bleaching agent to dental surfaces is to directly coat the dental surface with the bleaching agent.

At this time, fabric, paper, glass cloth, ceramic paper, an organic gel, an inorganic gel, or the like can be impregnated with the bleaching agent of the present invention, that is, a solution or paste of the aqueous hydrogen peroxide and titanium dioxide having photocatalytic action, and the impregnated product can be applied to the dental surface and irradiated with light. Other suitable methods and means can also be used, such as a method in which the aforementioned bleaching agent is supported on a suitable carrier, and is fitted or applied to a tooth or row of teeth.

The bleaching agent of the present invention comprises the combined use of the two aforementioned ingredients as active ingredients, which can be used in the form of a solution/paste comprising a blend of the ingredients. The ingredients may also be used in combined form as separate ingredients. The configuration is not particularly limited. A trace amount of iron ions in a concentration of about several ppm can also be blended as needed, so as to allow the bleaching effects to be further enhanced.

Discolored teeth can be bleached with the aforementioned bleaching agent by repeatedly applying a solution or paste of a titanium dioxide powder and 3% or less aqueous hydrogen peroxide to a dental surface, for example, and irradiating the coated area. The number of times the material is applied and irradiated may be suitably adjusted according to how light or heavy the staining is. The aforementioned solution or paste should usually be applied by coating or the like using fresh solution or paste about every 15 to 20 minutes. The interval and frequency should be suitably determined according to the state of the teeth.

The bleaching agent of the present invention is effective for bleaching both pulpless teeth and vital teeth, and produces pronounced effects while allowing the teeth to be safely and easily bleached.

The primary action of the bleaching agent in the present invention is bleaching action based on the synergistic action of the titanium dioxide photocatalyst and low concentration aqueous hydrogen peroxide (for example, 6% or less, and preferably 3% or less, aqueous hydrogen peroxide).

When the titanium dioxide photocatalyst is irradiated with light, electrons and positive holes are produced, reacting with hydrogen peroxide to produce active oxygen. The active oxygen has far greater oxidizing power than ozone, and can oxidize nearly all organic materials into carbon dioxide. Even when n type semiconductor titanium powder with a relatively substantial band gap is used in the form of a solution with 3% aqueous hydrogen peroxide, for example, light radiation readily results in the production of active oxygen having potent oxidizing power, ensuring higher levels of charge separation, electron hole mobility, reactivity with protons or hydroxyl groups, or the like than when used alone, so that synergistic action is produced in addition to the oxidizing action of the 3% aqueous hydrogen peroxide itself.

The titanium dioxide powder that is used comprises, for example, ultrafine particles with a particle diameter of 5 to 60 nm. As a result of the ultrafine particles or the impurity levels of the impurities contained therein, visible rays can be generated through the photocatalytic action produced only by irradiation with UV rays of a wavelength of 380 nm or less having energy corresponding to the band gap of the titanium dioxide due to the aforementioned synergistic action and the like.

Dental staining factors are broadly classified into the following extrinsic and intrinsic factors.

Extrinsic Staining Factors
- I. Food ingredients (pigments)
  - hard water (containing iron, etc.)
  - refreshment beverages (such as tea, coffee, cocoa, soft drinks, and red wines)
- II. Pigments produced by oral flora
- III. Tobacco
- IV. Metal deposition
- V. Chemicals (disinfectants)

Intrinsic Factors
- I. Pulp necrosis
- II. Bleeding in dental pulp (from external trauma, following pulpectomy, arsenious acid)
- III. Root canal filler components (amalgalms, silver powder, iodine, etc.)

IV. Tooth decay, rheumatic fever

V. Metabolic disorders (hereditary) ochronosis kaptonuria congenital dyserythropoietic anemia erythroblastosis neonatorum icterus gravis neonatorum VI. chemicals (antibiotics, root canal therapeutics)

VII. hard water (containing fluorine)

The aforementioned staining factors are caused by a variety of pigments, iron salts, tannic acid, chlorhexidine, benzalkonium chloride-chlorhexidine, and cyclones. Such colored substances adhere to tooth enamel and dentine.

A solution of titanium oxide and, for example, 6% or less, and preferably 3% or less, aqueous hydrogen peroxide penetrates between the enamel prisms and dentine, and bleaching is brought about as colored substances are degraded by the oxidative and reductive action of the photocatalyst. The bleaching method of the present invention affords high bleaching effects for discolored teeth caused by both intrinsic and extrinsic factors.

Examples of the light source (radiation instrument) used in the present invention generally include white heating lamps, fluorescent light lamps, halogen lamps, xenon lamps, mercury lamps, and UV lamps, although LED (light-emitting diodes), semiconductor lasers, lights (penlights), and the like are preferred for their safety, convenience, and bleaching effects. Preferred radiation light is light including an abundance of short wavelength light with substantial energy such as UV rays because of their oxidizing action and the active oxygen produced by the photocatalytic action, but since UV rays can be harmful to humans, causing inflammation and cancer, visible light is preferred in the interests of safety, among which violet light having substantial energy is ideal, followed by blue light.

In the present invention, the aforementioned bleaching agent, means for applying the bleaching agent (applicators, etc.), radiation instruments, other chemical agents, other dental treatment materials, instruments, and the like can be suitably combined to produce a system (kit) for bleaching teeth.

DESCRIPTION OF THE PREFERRED EMBODIMENTS

The present invention is described in further detail below with reference to examples, but the present invention is not in any way limited to these examples alone.

EXAMPLE 1

(1) Preparation of Bleaching Agent 0.3 g of anatase type $TiO_2$ powder with a particle diameter of 7 nm was blended with 1 mL each of a) 0.5% aqueous hydrogen peroxide, b) 1.5% aqueous hydrogen peroxide, and c) 3% aqueous hydrogen peroxide, and the ingredients were kneaded and dispersed to prepare solutions of titanium dioxide and aqueous hydrogen peroxide. 1 g of anatase type $TiO_2$ powder with a particle diameter of 7 nm was similarly used to prepare a d) paste of 3% aqueous hydrogen peroxide. The products were then housed in containers shielded from light, giving bleaching agents.

(2) Preparation of System for Bleaching Teeth

The aforementioned bleaching agents were housed in containers together with an applicator, radiating instrument (using LED violet light), and preparatory utensils, so as to prepare a system (kit) for bleaching teeth.

(3) Bleaching Discolored Teeth

The aforementioned bleaching agents were used to bleach discolored teeth by the following procedure.

1) Tartar, calculus, tar, and the like were removed with an ultrasonic scaler as preparation.

2) The surfaces of the teeth were cleaned by a common method using a rubber cap or the like, and were then dried.

3) The teeth were then temporarily moisture-proofed.

4) The dental surface was coated with a solution of titanium oxide and 3% aqueous hydrogen peroxide, and irradiated with visible light.

5) The treatment was 60 minutes. Fresh solution was applied and irradiated every 15 to 20 minutes.

6) Bleaching was completed with about 1 treatment when the discoloration was mild, with about 2 to 3 treatments when the discoloration was moderate, and with about 4 to 5 treatments when the discoloration was pronounced.

(4) Results

Table 1 shows the results obtained with the aforementioned bleaching agents. It is apparent from Table 1 that teeth with mild discoloration (F1) enjoyed considerable bleaching effects after about 1 procedure described above, and that teeth with moderate discoloration (F2 to F3) enjoyed considerable bleaching effects after about 2 to 3 times. Teeth with pronounced discoloration (F4) were bleached after about 4 to 5 times. The aforementioned bleaching effects were long-lasting, with no need for return treatment.

Since the bleaching agent of the present invention provides excellent bleaching effects through the synergism between the bleaching action based on the titanium oxide photocatalyst and the bleaching action of the aqueous hydrogen peroxide, there are no operational restrictions such as those in the case of conventional, highly toxic 30 to 35% aqueous hydrogen peroxide. It may also be understood that the bleaching agent of the present invention can be used for both pulped and pulpless teeth, since it is highly safe.

Compared, in terms of oxidizing energy, to conventional bleaching agents based on aqueous hydrogen peroxide, the bleaching agent in the present invention can be seen to have rapidly resulted in about 2.9 times or more greater bleaching effects.

It is also evident from Table 1 that lower aqueous hydrogen peroxide concentrations tended to require a longer period of time.

The bleaching effects were also enhanced, irrespective of $H_2O_2$ concentration, by mixing a solution containing trace amounts of iron salts with the aforementioned bleaching agent applied to the teeth, and then irradiating the coated portion.

TABLE 1

| Sample No. | Site | Degree of discoloration | Time of Treatment (min) | Effects | Return |
|---|---|---|---|---|---|
| 1 | 3+3 | F1 | 60 | +++ | − |
| 2 | 3+3 | F1 | 60 | +++ | − |
| 3 | 3+3 | F1 | 70 | +++ | − |
| 4 | 3+3 | F1 | 50 | +++ | − |

TABLE 1-continued

| Sample No. | Site | Degree of discoloration | Time of Treatment (min) | Effects | Return |
|---|---|---|---|---|---|
| 5 | 3 ┼ 3 | F2 | 110 | +++ | − |
| 6 | 3 ┼ 3 | F2 | 120 | +++ | − |
| 7 | 3 ┼ 3 | F2 | 110 | +++ | − |
| 8 | 3 ┼ 3 | F2 | 120 | +++ | − |
| 9 | 3 ┼ 3 | F2 | 120 | +++ | − |
| 10 | 3 ┼ 3 | F2 | 110 | +++ | − |
| 11 | 3 ┼ 3 | F2 | 120 | +++ | − |
| 12 | 3 ┼ 3 | F2 | 120 | +++ | − |
| 13 | 3 ┼ 3 | F2 | 120 | +++ | − |
| 14 | 3 ┼ 3 | F2 | 110 | +++ | − |
| 15 | 21 \| 2 | F3 | 180 | ++ | − |
| 16 | 1 \| 12 | F3 | 180 | +++ | − |
| 17 | 1 \| 1 | F3 | 200 | ++ | − |
| 18 | \| 2 | F4 | 400 | ++ | − |
| 19 | 1 \| | F4 | 260 | +++ | − |

In Table 1, bleaching agent a) was used in Samples 18 and 19, bleaching agent b) was used in Samples 15 through 17, bleaching agent c) was used in Samples 1 through 6 and 9 through 12, and bleaching agent d) was used in Samples 7, 8, 13, and 14.

The degree of discoloration was classified as follows.
F1: entire crown uniformly colored light yellow, brown, and gray, without striations.
F2: entire crown uniformly colored a deeper shade than F1, with no striations.
F3: deep gray, bluish gray, with striations.
F4: entire crown extremely purple and grayish purple.
The effects were rated in the following manner.
+++: bleaching effects resulted in considerable whitening.
++: bleaching effects were obtained, but slight staining (discoloration) remained.

EXAMPLE 2

(1) Bleaching of Discolored Teeth by Application of Bleaching Agent and Irradiation Dental surfaces (of extracted teeth) were coated with a bleaching agent (solution) comprising 0.5 g $TiO_2$ powder mixed with 3% $H_2O_2$, and were irradiated with visible light. The coating and irradiation were repeated in the same manner as in Example 1.

As a control, discolored teeth (extracted teeth) were coated with 3% $H_2O_2$ by itself, and irradiated with visible light and UV rays continuously for 10 hours.

(2) Bleaching Agent Configuration and Treatment

Following common dental surface cleaning, attempts were made to bleach discolored teeth by applying and irradiating an agent according to a) through c) below.

a) The surface of teeth were coated with the aforementioned $TiO_2$–3% $H_2O_2$ solution using an applicator, and then irradiated with visible light.

b) Dental surfaces were covered with paper ceramic containing $TiO_2$ powder (by Noritake Company Ltd.). 3% $H_2O_2$ was then applied thereon using an applicator, and the material was irradiated.

c) Dental surfaces were coated with a paste comprising $TiO_2$–3% $H_2O_2$ (1.2 g/mL) as active ingredients, and were irradiated.

(3) Concentration of Aqueous Hydrogen Peroxide

The concentration of aqueous hydrogen peroxide was varied within the range from 0.1% to 35%, and attempts were made to bleach discolored teeth by applying and irradiating (visible light) the material in the same manner as above.

Extremely discolored teeth were coated on the surface with 30 to 35% $H_2O_2$—$TiO_2$ solutions and irradiated with UV rays.

30 to 35% $H_2O_2$ is corrosive on the mucosa, skin, eyes, and respiratory tract, and UV rays also have deleterious action on the human body, so adequate protective measures were taken during treatment.

(4) Irradiation

The type of radiated light (wavelength of 250 to 600 nm) was varied in attempts to bleach discolored teeth by applying and irradiating the material in the same manner as above.

(5) Effects

Considerable bleaching effects were noted after about 2 hours in (1) above. Except for discolored teeth resulting from pulp necropathy, the bleaching effects as a whole were excellent. Excellent bleaching effects were also obtained by adjusting the irradiation time according to the degree of discoloration. It was also possible to control adjustments to suitable levels by adjusting the method and time. No bleaching effects were noted in controls.

There were no significant differences in bleaching effects due to bleaching agent configuration or method in (2) above. Technicians can accordingly make their selections by determining the workability depending on the site of the discolored teeth.

In (3) above, the 5% to 35% $H_2O_2$ solutions did not significantly differ from 3% or lower solutions.

Solutions of 0.1 to 3% $H_2O_2$ tended to take a longer time as the concentration became weaker. The time needed can thus be adjusted by adjusting the $H_2O_2$ concentration.

In (4) above, shorter wavelengths tended to result in shorter times. However, it may be seen that violet visible light was particularly effective when considered overall in terms of the toxicity of UV rays, the differences in the time needed, safety, and the like.

As described above, the present invention relates to a bleaching agent for bleaching discolored teeth based on the photocatalytic action that is produced when the agent is applied to the surface of discolored teeth and is irradiated, comprising as active ingredients a combination of aqueous hydrogen peroxide and titanium dioxide producing photocatalytic action when irradiated. The present invention is extremely useful for cosmetic improvements of teeth because of the following effects: (1) the ability to provide a novel bleaching agent for discolored teeth; (2) the ability to bleach both vaital teeth and pulpless teeth; (3) higher safety, better workability, and rapid bleaching effects; (4) alleviation of mental distress on treated patients; (5) the ability to control the level of color adaptation; and (6) the ability to select improvements in color adaptation desired by the treated patient.

What is claimed is:

1. A method for bleaching discolored teeth comprising applying a solution or paste or both comprising a titanium dioxide powder and hydrogen peroxide solution onto the surface of the discolored teeth, and irradiating the discolored teeth with light, thereby bleaching the teeth by resultant photocatalytic action.

2. The method for bleaching discolored teeth according to claim 1, wherein said irradiating light is violet or blue visible light.

3. The method for bleaching discolored teeth according to claim 1, which comprises:
   a) cleaning surfaces of the discolored teeth;
   b) moisture-proofing said cleaned surfaces; and
   c) coating said moisture-proofed surfaces with said solution or paste or both of said titanium dioxide powder and said hydrogen peroxide, and irradiating said coated surfaces with visible light.

4. The method for bleaching discolored teeth according to claim 3, wherein step c) is repeated, whereby fresh paste or solution or both is applied and irradiated every 15 to 20 minutes.

5. The method for bleaching discolored teeth according to claim 4, wherein step c) is repeated 2 or 3 times.

6. The method for bleaching discolored teeth according to claim 5, wherein step c) is repeated 4 or 5 times.

7. The method for bleaching discolored teeth according to claim 1, wherein said solution or past further comprises trace amounts of iron salts.

8. A bleaching composition for bleaching discolored teeth by photocatalytic action produced by irradiation with light, wherein said bleaching composition comprises as active ingredients a combination of 6% or less hydrogen peroxide solution and crystalline titanium dioxide photocatalyst, wherein said photocatalyst produces the photocatalytic action and reacts with the hydrogen peroxide to produce active oxygen when irradiated with light.

9. The bleaching composition according to claim 8, which consists essentially of a solution/paste of titanium dioxide with a particle diameter of about 5 to 60 nm and 3% or less hydrogen peroxide solution.

10. The bleaching composition according to claim 8, which further comprises trace amounts of iron salts.

11. A method for producing a bleaching composition for bleaching discolored teeth by photocatalytic action produced by irradiation with light, which method comprises:

blending 6% or less hydrogen peroxide solution with a crystalline titanium dioxide photocatalyst powder, wherein said photocatalyst producing the photocatalytic action and reacts with hydrogen peroxide to produce active oxygen when irradiated with light.

12. The method for producing a bleaching composition according to claim 11, wherein 3% or less hydrogen peroxide solution is blended with the crystalline titanium dioxide photocatalyst powder.

13. The method for producing a bleaching agent according to claim 11, wherein the crystalline titanium dioxide photocatalyst powder is anatase-type titanium dioxide.

14. A system for bleaching teeth, comprising a combination of a bleaching composition, materials or device for applying said bleaching composition, irradiating device, and optionally other dental treatment materials, wherein the bleaching composition comprises as active ingredients a combination of 6% or less hydrogen peroxide solution and crystalline titanium dioxide photocatalyst, said photocatalyst producing the photocatalytic action and reacting with the hydrogen peroxide to produce active oxygen when irradiated with light.

15. The system for bleaching teeth according to claim 14, wherein the radiating device generates visible violet light.

16. The system for bleaching teeth according to claim 15, wherein the radiating device generates LED violet light.

* * * * *